United States Patent
Wilson et al.

(10) Patent No.: US 8,817,266 B2
(45) Date of Patent: Aug. 26, 2014

(54) GAS SEPARATORS WITH FIBER OPTIC SENSORS

(71) Applicant: Baker Hughes Incorporated, Houston, TX (US)

(72) Inventors: Brown Lyle Wilson, Tulsa, OK (US); Donn J. Brown, Broken Arrow, OK (US); Ketankumar K. Sheth, Tulsa, OK (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 13/971,219

(22) Filed: Aug. 20, 2013

(65) Prior Publication Data

US 2014/0000345 A1  Jan. 2, 2014

Related U.S. Application Data

(63) Continuation-in-part of application No. 13/314,010, filed on Dec. 7, 2011, now Pat. No. 8,537,364.

(51) Int. Cl.
| | |
|---|---|
| *G01N 21/55* | (2014.01) |
| *G01N 21/00* | (2006.01) |
| *G01D 5/26* | (2006.01) |
| *G01D 5/353* | (2006.01) |
| *G01N 21/47* | (2006.01) |

(52) U.S. Cl.
CPC ............... *G01N 21/00* (2013.01); *G01D 5/268* (2013.01); *G01D 5/35383* (2013.01); *G01N 21/47* (2013.01)
USPC .......................................... 356/446; 356/445

(58) Field of Classification Search
CPC  E21B 47/123; E21B 47/122; E21B 47/02216
See application file for complete search history.

(56) References Cited

U.S. PATENT DOCUMENTS

| | | | |
|---|---|---|---|
| 6,888,124 B1 | 5/2005 | Smith | |
| 6,913,079 B2 | 7/2005 | Tubel | |
| 7,208,855 B1 | 4/2007 | Floyd | |
| 2003/0236626 A1 | 12/2003 | Schroeder et al. | |
| 2004/0141420 A1 | 7/2004 | Hardage et al. | |
| 2007/0041019 A1 | 2/2007 | Schmidt | |
| 2007/0272406 A1 | 11/2007 | McCoy et al. | |
| 2009/0065202 A1 | 3/2009 | Brown et al. | |
| 2011/0002795 A1* | 1/2011 | Brookbank | 417/63 |
| 2011/0139447 A1 | 6/2011 | Ramos et al. | |
| 2012/0026482 A1 | 2/2012 | Dailey | |
| 2012/0073804 A1* | 3/2012 | Harman et al. | 166/250.01 |
| 2012/0179378 A1 | 7/2012 | Duncan et al. | |

* cited by examiner

*Primary Examiner* — Michael P Stafira
(74) *Attorney, Agent, or Firm* — Shawn Hunter (57) ABSTRACT

Devices and methods for detecting operational parameters associated with a gas separator used in an electric submersible pump in a wellbore. A fiber optic sensing arrangement is used to detect the operational parameter and includes a fiber optic signal processor and an optic fiber that is associated with the gas separator to provide a signal indicative of the parameter to the signal processor.

20 Claims, 7 Drawing Sheets

GAS SEPARATORS WITH FIBER OPTIC SENSORS

BACKGROUND OF THE INVENTION

1. Field of the Invention

The invention relates generally to gas separators of the type that are used within electrical submersible pumps (ESP's). In particular aspects, the invention relates to techniques for monitoring operational parameters of gas separators.

2. Description of the Related Art

Electrical submersible pumps (ESPs) are routinely used in the production of hydrocarbon from wells. A typical ESP includes a centrifugal pump that is driven by a submersible electric motor. A gas separator is used to remove gases from production fluid before the production fluid enters the pump since such gases will degrade the performance of the pump. A gas separator draws in production fluid and induces fluid rotation, centrifugally separating heavier from lighter components. These components are split into separate flow paths, with lighter components exiting to the casing annulus and heavier components to the pump entrance. A gas separator is generally much simpler in construction and operation because it does not require a pressure barrier or fluid barrier between the internal portions of the separator and the casing annulus.

SUMMARY OF THE INVENTION

The present invention provides devices and methods to monitor or measure operational parameters associated with a gas separator during operation. In described embodiments, at least one interior chamber or section of the gas separator is provided with one or more optic fibers to measure operational parameters including pressures, temperatures, vibrations in the bearings, leakage of well fluid/moisture detection, thrust, proximity probes for clearance, viscosity, fluid density and gas content.

In one described embodiment, an optic fiber having distributed measuring capabilities runs through the at least one chamber. Bragg gratings can be used to allow detection of a selected operating parameter at one or a number of discrete points along the fiber. As a result, sensing of the selected parameter at a number of distinct points within the gas separator is possible. In described embodiments, the optic fiber can be disposed between the outer housing of the gas separator and an interior liner.

According to described embodiments, flanged, bolted connections are used to interconnect sections of the gas separator as well as to affix the gas separator to adjacent components within the electrical submersible pump. The use of flanged, bolted connections allows the tool to be made up and disassembled without having to unthread the components and thereby damage the fibers.

According to other particular embodiments, optic fibers are directed into the gas separator from the radial exterior of the gas separator. The axial ends of the fibers function as point sensors to detect a selected operational parameter associated with the gas separator.

The operational parameters that are sensed can be continuously monitored for reliability and performance measurement of the gas separator to monitor separator efficiency and well fluid composition. Thus, the devices and methods of the present invention can be used to increase the run life and be used to predict failures of portions of the separator, which can increase the efficacy of preventative maintenance. Also, operating parameters of the gas separator, such as speed, back pressure, etc. may be modified, based upon detected values, to enhance production.

BRIEF DESCRIPTION OF THE DRAWINGS

For a thorough understanding of the present invention, reference is made to the following detailed description of the preferred embodiments, taken in conjunction with the accompanying drawings, wherein like reference numerals designate like or similar elements throughout the several figures of the drawings and wherein.

DETAILED DESCRIPTION OF THE PREFERRED EMBODIMENTS

Figure 1:
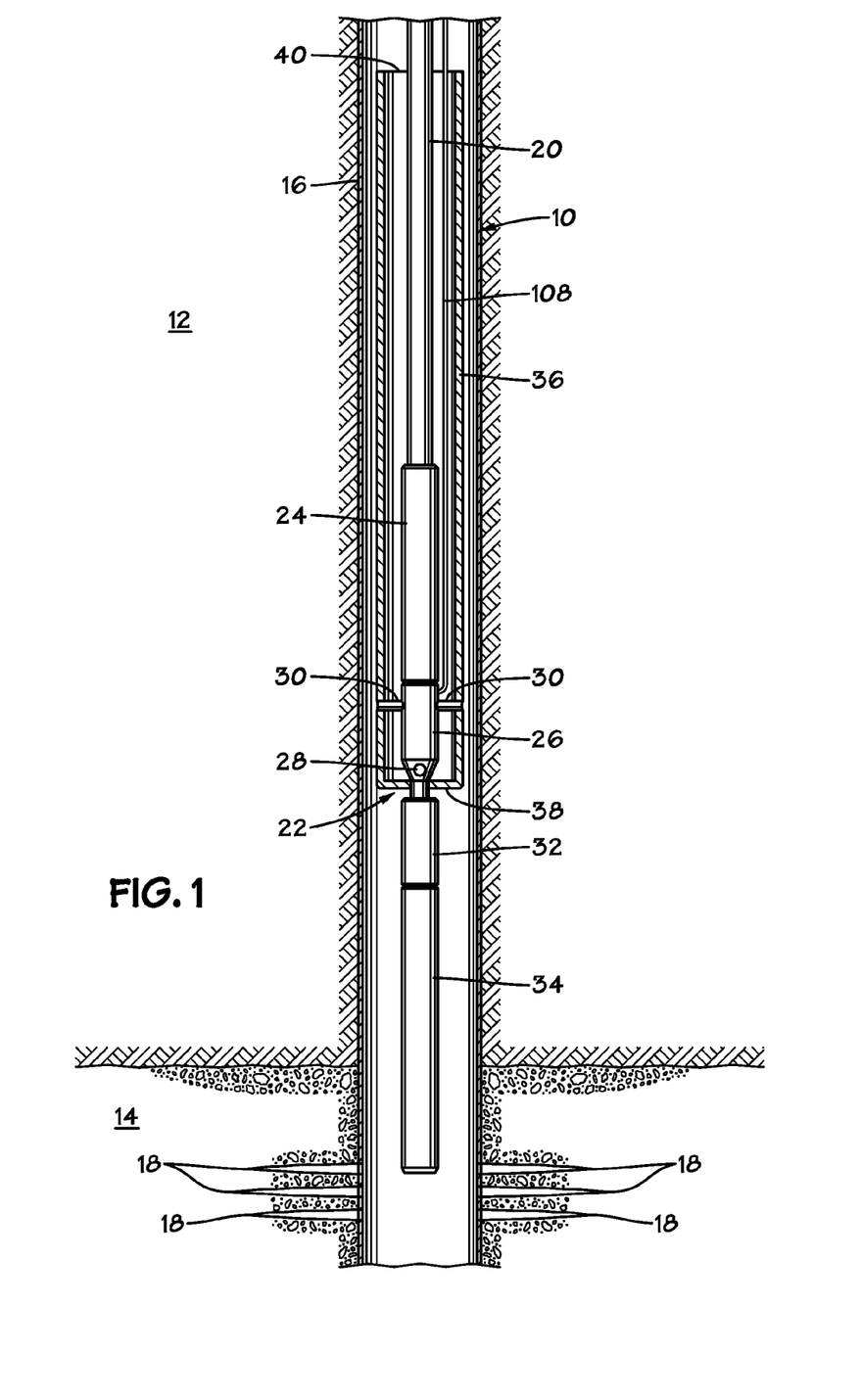
FIG. 1 is a side, cross-sectional view of an exemplary wellbore containing an electric submersible pump.

FIG. 1 depicts an exemplary wellbore 10 that has been drilled through the earth 12 down to a subterranean hydrocarbon formation 14. The wellbore 10 has metallic casing 16 of a type known in the art. Perforations 18 are disposed through the casing 16 and into the formation 14.

Production tubing 20 is disposed within the wellbore 10, having been run in from the surface in a manner known in the art. The production tubing 20 may be a string of production tubing members that are interconnected by threaded or it may be coiled tubing. An electric submersible pump (ESP) assembly 22 is affixed to the lower end of the production tubing 20. The exemplary ESP assembly 22 includes a centrifugal pump 24 which is affixed at its lower end to a gas separator 26. The gas separator 26 has a fluid intake port 28 through which fluid is drawn. The gas separator 26 functions to separate and remove gas from production fluid prior to the production fluid entering the pump 24. Gas discharge tubes 30 extend radially outwardly from the gas separator 26 to allow discharge of separated gas.

A seal section 32, of a type known in the art, interconnects the lower end of the gas separator 26 to a motor 34. The motor 34 is of a type known in the art and may be a three-phase electrical motor. The seal section 32 is also of a type known in the art and is capable of equalizing the pressure of the lubricant contained within the motor 34 with well fluid on the exterior of motor 34.

A shroud 36 radially surrounds the pump 24 and gas separator 26. In the depicted embodiment, the shroud 36 has a closed lower end 38 and an open upper end 40. Gas discharge tubes 30 pass through the shroud 36 to permit removed gas to be disposed outside of the shroud 36. Further details relating to the construction and operation of electric submersible pump assemblies and gas separators can be found in U.S. Patent. Publication No. US 2009/0065202 which is owned by the assignee of the present application. U.S. Patent Publication No. US 2009/0065202 is hereby incorporated by reference in its entirety.

Figure 2:
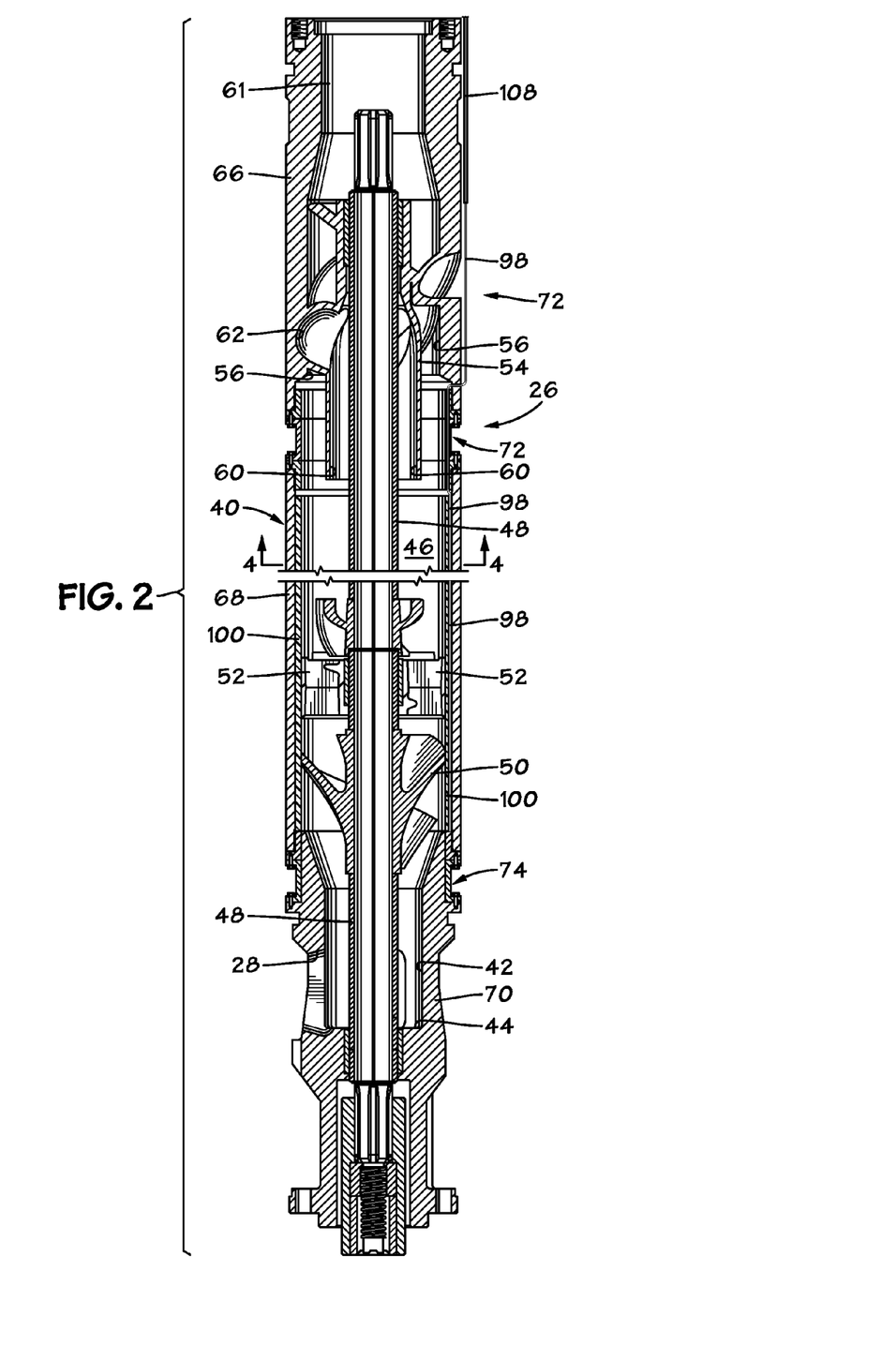
FIG. 2 is a side, cross-sectional view of an exemplary gas separator used with the electrical submersible pump of FIG. 1.

FIG. 2 depicts an exemplary gas separator 26 in greater detail. The gas separator 26 has a generally cylindrical housing 41 which defines an intake chamber 42 proximate its closed lower end 44. The fluid inlet 28 provides fluid communication between the intake chamber 42 and an area external to the gas separator 26. A gas separator chamber 46 is also defined within the housing 40 above the intake chamber 42.

A rotatable shaft 48 extends through Intake chamber 42 and into the gas separator chamber 46. The shaft 48 is coupled to a rotatable shaft within the seal section 32, which is turn is rotated by the motor 34. Rotation of the shaft 48 causes lighter gases to be removed from production fluid which enters the separator chamber 46 through fluid inlet 28. A type of inducer known as a high angle auger 50 is mounted to shaft 48 for rotation therewith. Auger 50 draws well fluid in through intake port 28 and intake chamber 42 and pumps it upwardly. Vanes 52 are mounted to the shaft 48 above the auger 50 to impart centrifugal force to the well fluid. The centrifugal force forces heavier well fluid components outwardly toward housing 40 while the lighter components remain in a central area surrounding shaft 41 and are flowed axially upwardly to the pump 24.

Cross-over member 54 has a plurality of liquid passages 56. Each liquid passage 56 has a lower end located radially outwardly proximate the housing 40 and an upper end that is radially inward from the lower end to discharge heavier components into a central chamber 58. Central chamber 58 leads to the entrance of pump 24. Cross-over member 54 also has a plurality of gas passages 60. Each gas passage 60 has a lower end that is located radially inwardly near shaft 41 and an upper end that is radially farther outward from shaft 41 than the lower end. Gas passages 60 are fluid outlet ports that discharge the lighter components into an annular chamber 62 which would be affixed to gas discharge tubes 30. Heavier production fluid components are flowed axially upwardly through fluid passage 61 toward the pump 24.

It is noted that, in the depicted embodiment, the housing 40 of the gas separator 26 is made up of an upper housing section 66, central housing section 68, and a lower housing section 70. The housing sections 66, 68, 70 are preferably affixed to one another by a bolted make-up connection 72 or 74. Exemplary bolted make-up connection 72 is depicted in greater detail in FIG. 3. Preferably, make-up connection 74 has the same construction as make-up connection 72. The make-up connection 72 includes upper and lower end rings 76, 78. Each of the end rings 76, 78 has a threaded portion 80 that is shaped and sized to be complimentary to threaded portions 82 of upper and central housing sections 66, 68. Each of the end rings 76, 78 also presents a threaded opening 84 which is shaped and sized to receive a threaded connector, such as a bolt. A base ring 86 is disposed axially between the two end rings 76, 78. The exemplary base ring 86 includes a central web portion 88 and two flanges 90, 92 which project radially outwardly from either axial end thereof. Bolts 94 pass thorough openings 96 in the flanges 90, 92 and into the openings 84 to secure the make-up connection 72 together. It is noted that, while only a single bolt 94 is shown, there are preferably a number of bolts 94 disposed through each of the flanges 90, 92 to secure each connection together. The make-up connections 72, 74 are useful to retrofit tools with existing threaded connection portions 82 to permit non-rotational connection.

Figure 3:
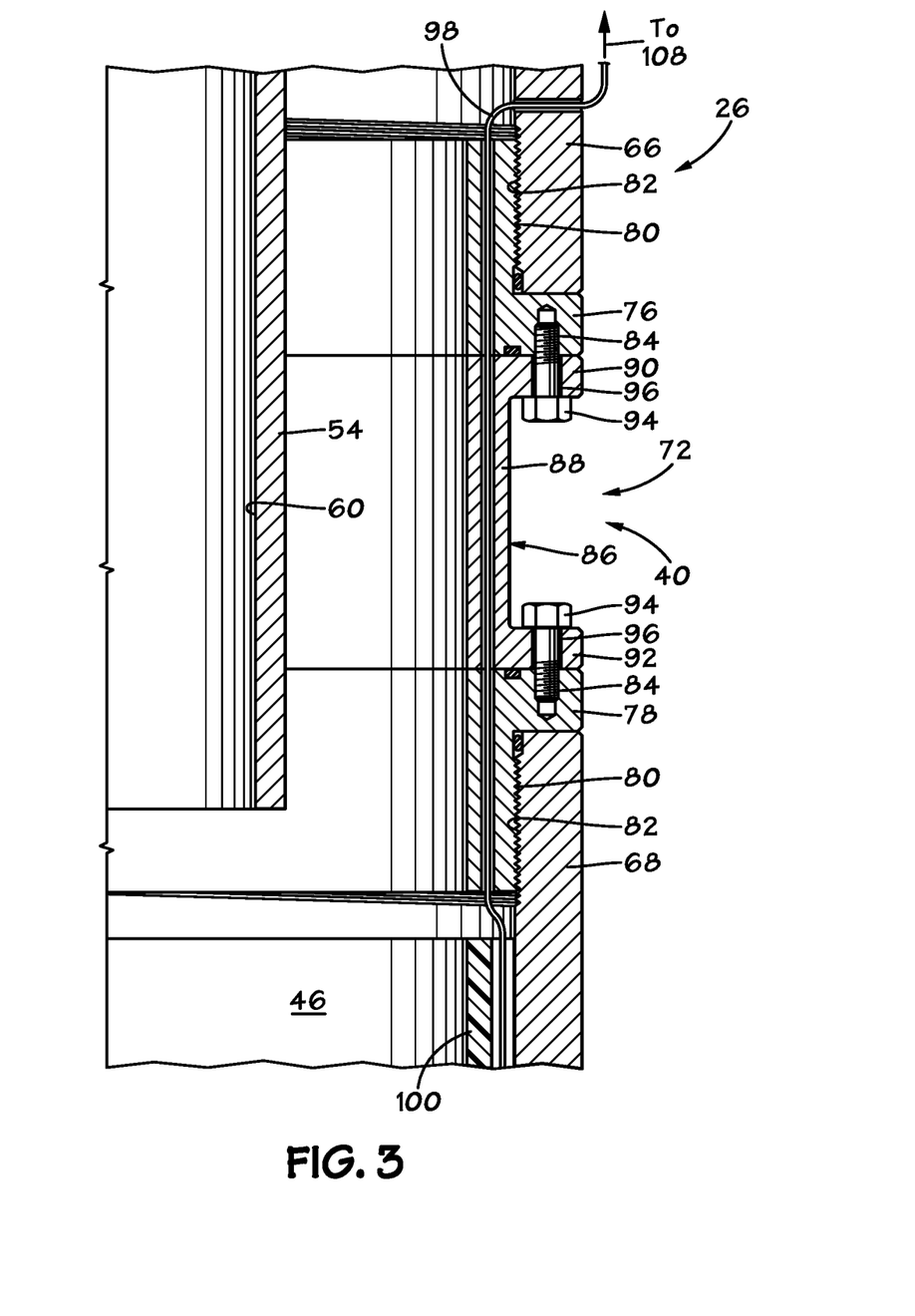
FIG. 3 is a side, cross-sectional view of an exemplary joint interconnecting sections of the gas separator shown in FIG. 2.

In practice, a gas separator 26 is provided with one or more flanged, bolted make-up connections 72, 74 by affixing the end rings 76 and 78 to the existing threaded portions 82 of the gas separator 26. If desired, anti-rotation locking mechanisms, of a type known in the art, may be used to prevent unthreading of the end rings 76, 78. Thereafter, holes are drilled or otherwise formed through the housing 40 in a generally axial direction to permit an optic fiber 98 to be passed through the housing 40. The optic fiber 98 is representative of any of the optic fibers described herein and can be of conventional construction to include a central axial core which is surrounded by cladding. The optic fiber 98 may also be radially surrounded by a protective sheath, as is known in the art, for protection of the fiber from physical hazards.

Figure 4:
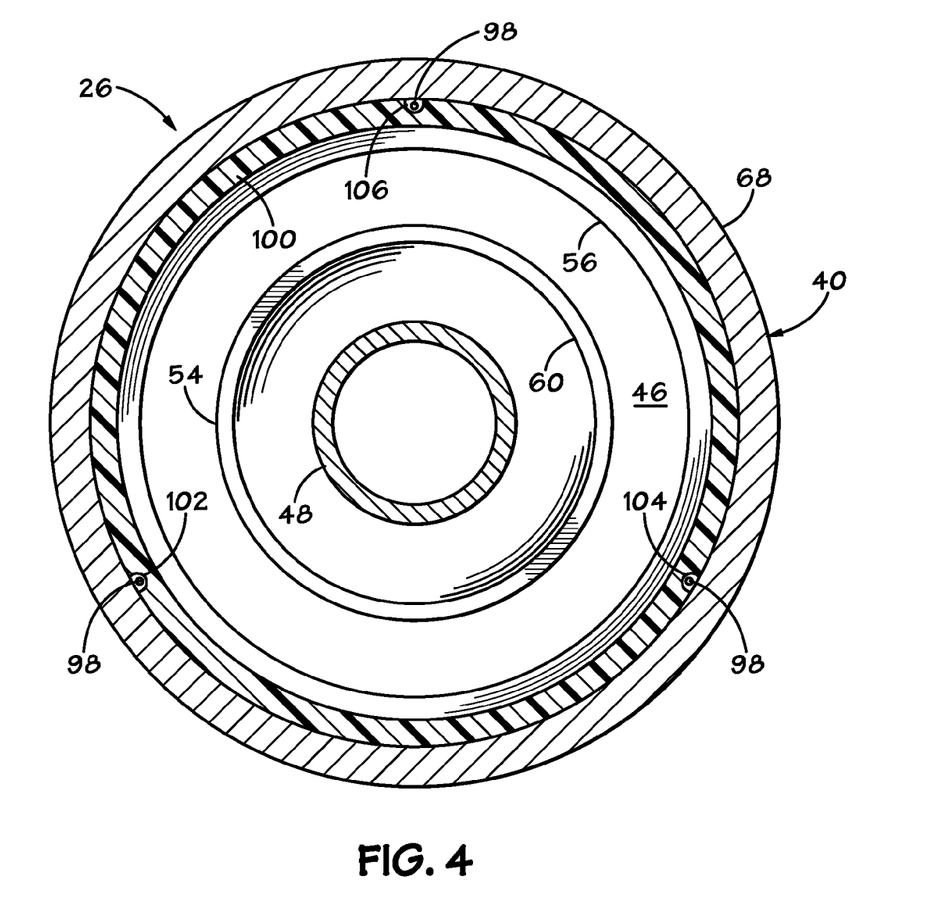
FIG. 4 is an axial cross-section taken along lines 4-4 in FIG. 2.

It is noted that the internal surfaces of a gas separator are largely all lined with corrosion-resistant and abrasion-resistant separator liner. An interior separator liner 100 is depicted lining the chamber 46 in FIGS. 2 and 4. The liner 100 may be formed of thermoplastic or another material that is suitable for resisting abrasion and corrosion. FIG. 4 is a cross-sectional vie taken along lines 4-4 in FIG. 2 and illustrates axial grooves 102, 104, 106 formed in the liner 100. In the depicted embodiment, there are three grooves 102, 104, 106, and they are spaced in a substantially equiangular manner about the outer circumference of the liner 100. Those of skill in the art should understand that there may be more or fewer than three grooves. One of more optic fibers 98 pass along each of the grooves 102, 104, 16 between the housing 40 and the liner 100 of the gas separator 26. As FIGS. 2 and 3 depict, the fiber 98 can pass through the housing 40 of the gas separator 26 proximate its upper end and be incorporated into a fiber optic cable 108 which will extend to processing equipment at the surface of the wellbore 10. The fiber optic cable 108 will typically house or protect multiple individual optic fibers or fiber bundles for their protection between the gas separator 26 and the surface of the wellbore 10. The fiber optic cable 108 is typically armored or otherwise capable of protecting the fibers encased within.

Figure 3A:
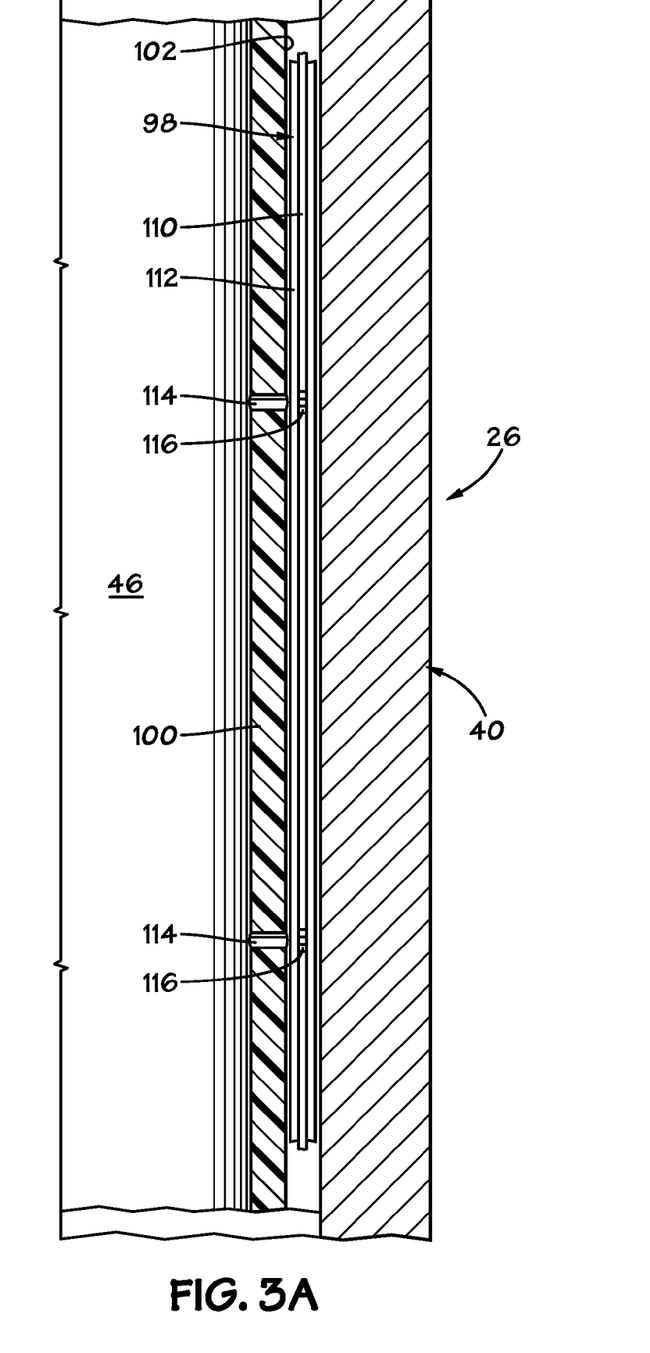
FIG. 3A is an enlarged, side cross-sectional view of a portion of a sidewall of the gas separator shown in FIGS. 2 and 3.

FIG. 3A is an enlarged side, cross-sectional view of a portion of the housing 40 and liner 100 of the gas separator 26. The exemplary optic fiber 98 is shown disposed within groove 102. The fiber 98 is shown to have a central axial core 110 which is radially surrounded by cladding 112. Lateral openings 114 are formed in the liner 100 and permit fluid communication between the separator chamber 46 and the groove 102 containing fiber 98.

Bragg gratings 116 are formed on the core 110 of the fiber 98. As is known in the art, Bragg gratings 116 may be created using UV laser or UV light in conjunction with a specific photomask to form a particular grating pattern. Each Bragg grating 116 functions as a sensor that exhibits a particular resonance feature which is tracked as the fiber 98 is subjected to strain or to temperature variations. Each Bragg grating 116 responds to a broadband optical signal (typically provided by the signal processor 138 depicted in FIG. 7) and further responds to the parameter being sensed, in order to provide a signal containing information about the parameter being sensed. As an optical pulse is provided to the fiber 98 by the signal processor 138, light is continuously backscattered as it propagates, as a result of Rayleigh scattering. The backscattered light is time-resolved by the signal processor 138 to provide a differential map of the spatial distribution of optical attenuation along the fiber 98. In embodiments wherein there are multiple Bragg gratings 116, a selected parameter can be measured at multiple, discrete points along the length of the fiber 98. In a particular exemplary embodiment, temperature is detected by each of the Bragg gratings 116 along the fiber 98, which will provide to an operator an indication of discrete hot spots along the axial length of the fiber 98. The use of multiple Bragg gratings 116 also allows the axial position of this heating to be determined as well.

According to an alternative embodiment, the Bragg gratings 116 are adapted to detect pressure or changes in pressure in the area proximate the fiber 98. The sensed data will provide an indication of the location(s) of high pressure areas along the length of the fiber 98.

According to a further alternative embodiment, the Bragg gratings 116 are adapted to allow detection of strain on the fiber 98. Strain can be converted to pressure or vibration depending upon the calibration of the measurement equipment being used (i.e., a fiber optic signal processor). Discrete distributed point measurements of strain along the length of the fiber 98 can provide indications of vibration or axial bending of the gas separator housing 40.

According to a further aspect of the present invention, the optic fiber 98 could be adapted to detect the viscosity of fluid flowing through the chamber 46 of the gas separator 26. Viscosity can be inferred from measurement of water/moisture content within a fluid which can be detected using the Bragg grating sensors 116 which are incorporated along the length of the fiber 98. Total internal reflection occurring at the core-cladding interface in an optic fiber provides an evanescent field in the cladding 112. This field presents an evanescent wave which propagates along the wave guide in the core 110 but which falls off exponentially in amplitude to a low value in a transverse distance of order one wavelength. The overall propagation of energy in the fiber is sensitive to evanescent wave absorption which occurs in the cladding 112.

Alternatively, sensors could be incorporated into the fiber 98 at predetermined locations within the chamber 46. These sensors would be created by removing the cladding 112 at the selected points and replacing it with a material whose absorption or fluorescence spectrum is sensitive to the absorption of an external chemical species. In one embodiment, approximately 50 cm sections of cladding 112 are removed and replaced by a gelatin film containing cobalt chloride. The salt changes color from blue to pink upon absorption of moisture, thus providing an indicator of relative humidity/moisture content. In particular embodiments, the absorption can be monitored at a wavelength of 670 nm and the signal normalized with respect to a backscattered signal at 850 nm which is unaffected by the color change.

Figure 5:
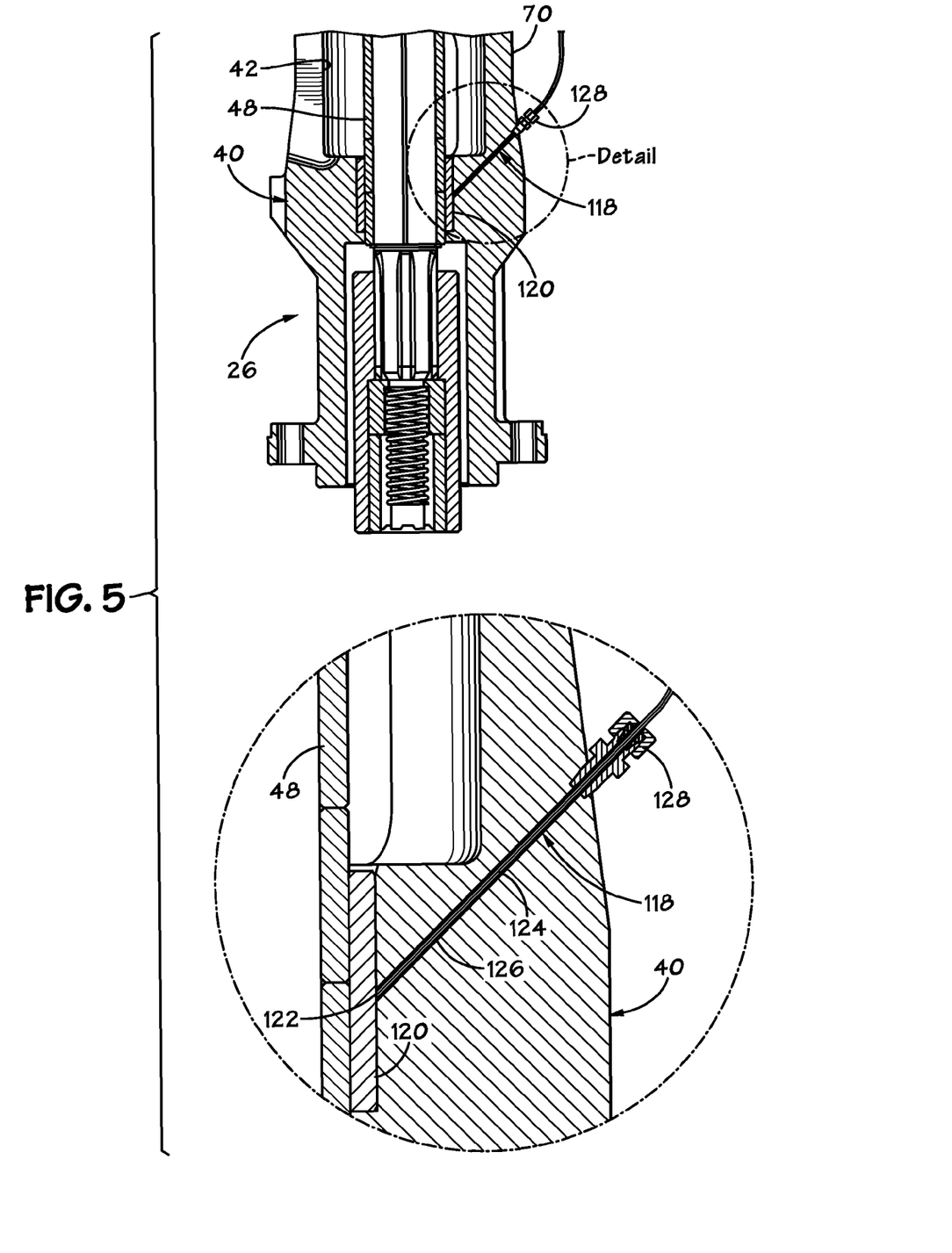
FIG. 5 illustrates exemplary placement of a fiber optic point sensor within a gas separator device.

FIG. 5 depicts lower portions gas separator 26 wherein an optic fiber sensor assembly 118 has been disposed through the housing 40 just below the intake chamber 42. In particular, the optic fiber sensor assembly 118 is disposed to sense one or more operating parameters associated with rotary bearing 120 between the rotary shaft 48 and the surrounding housing 40. It is noted that the location depicted in FIG. 5 is not intended to limit the invention to the placement of optic fiber sensor assemblies in any one location within a gas separator 26. Rather, the depicted location can represent other bearings and locations within the gas separator 26. The axial end 122 of optic fiber 124 functions as a point sensor to detect the one or more operating parameters. In a currently preferred embodiment, the optic fiber 124 is disposed into the housing 40 radially within a protective tube 126. The fiber 124 can be incorporated into the fiber optic cable 108 described previously to be routed to the surface of the wellbore 10. The protective tube 126 may be formed of PEEK (polyether ether ketone) or a similar rigid and resilient substance and prevents the fiber 124 from being inadvertently crushed or bent. A threaded fitting 128 is used to secure the optic fiber sensor assembly 118 within the housing 40.

The optic fiber sensor assembly 118 is primarily useful to detect vibration and or temperature proximate the bearing 120. It is noted that, while a fiber sensor assembly 118 is only depicted proximate a single bearing 120, there may be and preferably will be a similar fiber provided for other bearings within the gas separator 26. In preferred embodiments, the fiber 124 is used to detect proximity of the bearing 120 to the fiber axial end 122. In so doing, lateral or radial vibration of the bearing 120 can be detected and measured. An operator can monitor the condition of the bearings 70. Detection of temperature proximate the bearing 120 will permit monitoring of points of excessive friction resulting from the rotation of shaft 48. The fiber optic sensor assembly 118 may also be adapted to sense other operational parameters associated with the gas separator 26 as well.

Figure 6:
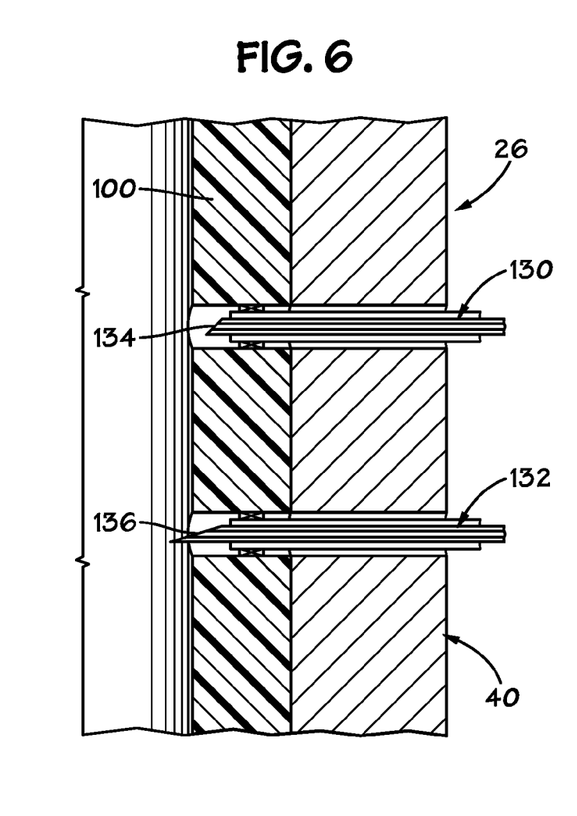
FIG. 6 is a side, cross-sectional view depicting oblique tip fiber optic sensors used to detect operational parameters associated with a gas separator.

Fiber optic sensor assemblies of the type shown in FIG. 5 could be adapted to measure fluid presence and viscosity or otherwise discriminate between flow of various fluids within the gas separator 26 by incorporating oblique tip sensing techniques. As depicted in FIG. 6, optic fibers 130 and 132 are disposed through gas separator housing 40 and liner 100. The fibers 130, 132 present axial ends 134, 136, respectively, that are each at an oblique angle to the longitudinal axis of its fiber 130 or 132. Each of the axial ends 134, 136 is preferably hard coated and wetted with fluid film. Oil is a preferred wetting film. The end 134 of fiber 130 is formed at an oblique angle of about 45 degrees. A silica fiber with an end face having an angle of about 45 degrees will provide 100% reflection when in gas and less than 1% reflection when disposed in oil or water. Thus, this fiber 130 can be used as a high contrast gas/liquid discriminator.

The end 136 of fiber 132 is formed at an oblique angle of about 73 degrees. A fiber with an end face having an angle of about 73% functions as a high contrast oil/non-oil discriminator, as the reflectivity becomes 100% when the fiber 132 is in gas or water and below 1% when in oil. If data from both fibers 130 and 132 is used together, three-phase discrimination of fluids can be achieved.

Figure 7:
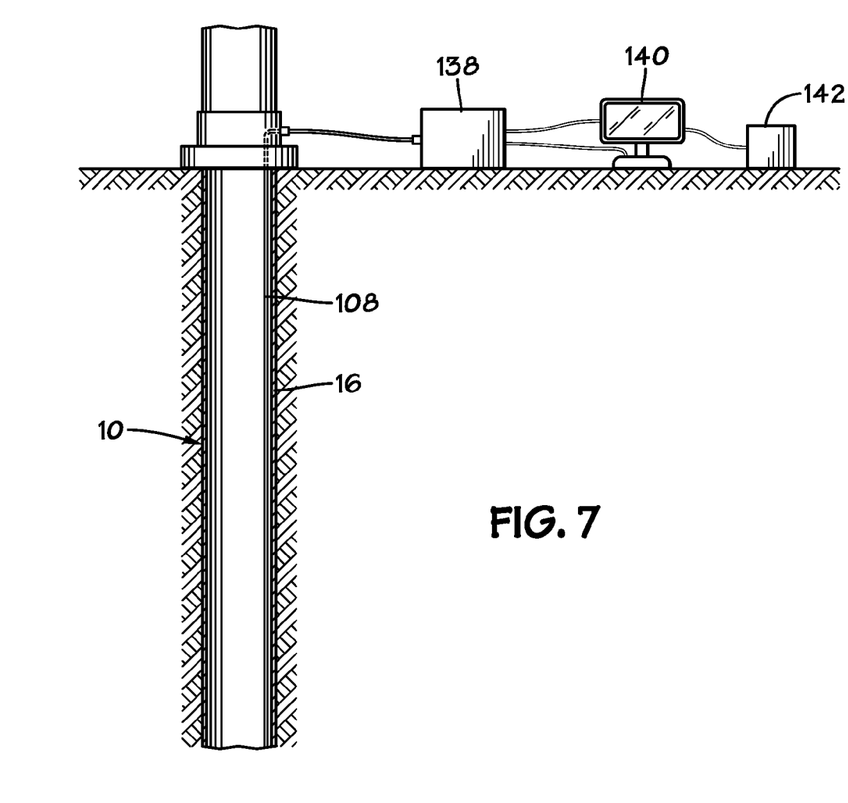
FIG. 7 depicts surface-based components that are operably interconnected with fiber optic sensors.

Other optical sensing techniques known in the art could also be used to detect the nature and attributes of fluids within the gas separator 26 and, thereby provide data to an operator which would permit the deduction of information relating to the viscosity of fluids within the gas separator 26 or the presence of contamination of fluids within. Near infrared attenuation ("NIR") relies on differences in the opacity of oil and water to the transmission of infrared light. Crude oil is composed of longer hydrocarbon chains and aromatics, such as $CH_2$ while natural gas consists of predominantly methyl groups (i.e., $CH_3$). Each radical has a distinctive near infrared attenuation absorption band. Therefore, it is possible to distinguish natural gas from crude oil based upon absorption level. Light from a broadband source, such as fiber optic signal processor 138, covering the near infrared wavelength range of around 1000 to about 1700 nm is transmitted along an optic fibers to a reflectance probe, of a type known in the art, which is immersed in fluid. Alternatively, induced fluorescence measurements could be used to determine the presence and attributes of oil, water, gas within portions of the gas separator 26. Any or all of the above-described techniques could be used to allow an operator to determine flow characteristics for fluids moving through the gas separator 26, such as flowrate and intrusion of undesirable fluids or particles (i.e., contamination).

FIG. 7 illustrates exemplary surface-based equipment to which the fiber optic cable 108 might be routed. The fiber optic cable 108 is operably interconnected with a fiber optic signal processor 138. In some embodiments, a suitable display 140 and recording device 142 are also associated with the signal processor 138. Generally, the fiber optic signal processor 138 includes a computer or microprocessor chip that is programmed to analyze an optical signal and send information relating to the optical signal to recordable storage in the recording device 142. The fiber optic signal processor 138 typically includes an optical time-domain reflectometer (OTDR) which is capable of transmitting optical pulses into the fiber optic cable 108 and analyzing the light that is returned, reflected or scattered therein. Changes in an index of refraction in optic fibers can define scatter or reflection points. Analyzing the collected return light can yield the distance to changes in the index of refraction. Thus, the OTDR can be used to detect the locations of sensed operating parameters along the length of the optic fibers that are carried within the fiber optic cable 108.

In accordance with the present invention, fiber optic sensors are used to detect one or more operational parameters associated with a gas separator. The operational parameters that can be measured include pressure, temperature, vibrations in the bearings, leakage of well fluid/moisture detection, thrust, proximity probes for clearance, viscosity, fluid density and gas content.

It should be understood that the invention provides a gas separator system that includes a gas separator device 26 that separates gas from production fluid and a fiber optic sensing arrangement to detect at least one operational parameter that is associated with the gas separator 26. The gas separator system also includes a fiber optic sensing arrangement that can detect at least one operational parameter associated with the gas separator 26. In described embodiments, the fiber optic sensing arrangement includes a fiber optic signal processor 138 and at least one optic fiber, such as fibers 98, 124, 130 or 132. The fiber optic sensing arrangement is capable of sensing such operational parameters as temperature, pressure, vibration, viscosity and fluid contamination.

It should also be understood that the invention provides methods for detecting an operational parameter associated with a gas separator 26 which includes the step of providing a fiber optic sensing arrangement having a fiber optic signal processor 138 and at least one optic fiber, such as fibers 98, 124, 130 or 132. The methods also include the step of operably associating the optic fiber with the gas separator 26 sot aht the optic fiber senses the operational parameter.

Those of skill in the art will recognize that numerous modifications and changes may be made to the exemplary designs and embodiments described herein and that the invention is limited only by the claims that follow and any equivalents thereof.

What is claimed is:

1. A gas separator system for use in separating gas from production fluid in an electric submersible pump, the gas separator system comprising:
a gas separator having an outer housing defining a separator chamber and having a fluid inlet and fluid outlet ports for evacuation of separated gases, and a central shaft that is retained within the housing and rotatable within to cause separation of gas from production fluid within the outer housing; and
an optic fiber sensing arrangement to detect at least one parameter associated with the gas separator.

2. The gas separator system of claim 1 wherein the fiber optic sensing arrangement comprises:
a fiber optic signal processor; and
an optic fiber operably associated with the fiber optic signal processor to provide to the fiber optic signal processor a signal indicative of the operational parameter.

3. The gas separator system of claim 1 wherein the operational parameters include at least one of the parameters from the group consisting of: temperature, pressure, vibration, viscosity and fluid contamination.

4. The gas separator system of claim 2 wherein the optic fiber has an axial length and includes one or more Bragg gratings for detection of the operational parameter along the axial length of the fiber.

5. The gas separator system of claim 4 wherein the optic fiber is further disposed between the outer housing and a liner within the outer housing.

6. The gas separator system of claim 2 wherein:
the optic fiber is disposed through the outer housing of the gas separator; and
the axial end of the optic fiber is used to detect the operational parameter.

7. The gas separator system of claim 6 wherein the axial end of the optic fiber is located proximate a bearing within the gas separator.

8. A gas separator system for use in separating gas from production fluid in an electric submersible pump, the gas separator system comprising:
a gas separator having an outer housing defining a separator chamber and having a fluid inlet and fluid outlet ports for evacuation of separated gases, and a central shaft that is retained within the housing and rotatable within to cause separation of gas from production fluid within the outer housing; and
an optic fiber associated with the gas separator to detect an operational parameter associated with the gas separator.

9. The gas separator system of claim 8 wherein the operational parameters include at least one of the parameters from the group consisting of: temperature, pressure, vibration, viscosity and fluid contamination.

10. The gas separator system of claim 8 wherein the optic fiber is operably associated with a fiber optic signal processor which is capable of transmitting optical pulses into the optic fiber and analyzing the light that is returned, reflected or scattered therein.

11. The gas separator system of claim 8 wherein the optic fiber has an axial length and includes one or more Bragg gratings for detection of the operational parameter along the axial length of the fiber.

12. The gas separator system of claim 11 wherein the optic fiber is further disposed between the outer housing and a liner within the outer housing.

13. The gas separator of claim 8 wherein:
the optic fiber is disposed through the outer housing of the gas separator; and the axial end of the optic fiber is used to detect the operational parameter.

14. The gas separator system of claim 13 wherein the axial end of the optic fiber is located proximate a bearing within the gas separator.

15. A method for detecting an operational parameter associated with a gas separator that separates gas from production fluid in an electric submersible pump, the method comprising the steps of:
providing a fiber optic sensing arrangement having a fiber optic signal processor and an operably associated optic fiber to provide a signal to the fiber optic signal processor that is indicative of a sensed operational parameter; and
operably associating the optic fiber with the gas separator so that the optic fiber senses the operational parameter.

16. The method of claim 15 wherein the operational parameters include at least one of the parameters from the group consisting of: temperature, pressure, vibration, proximity, viscosity and fluid contamination.

17. The method of claim 15 wherein:
   the gas separator includes an outer housing; and
   the optic fiber is disposed through the outer housing to detect the operational parameter at a location within the outer housing.

18. The method of claim 17 wherein the operational parameter is sensed using a Bragg grating.

19. The method of claim 17 wherein the operational parameter is sensed using an axial end of the optic fiber.

20. The method of claim 17 wherein the operational parameter is sensed proximate a bearing.

* * * * *